United States Patent [19]

Weijand

[11] Patent Number: 5,336,244
[45] Date of Patent: Aug. 9, 1994

[54] TEMPERATURE SENSOR BASED CAPTURE DETECTION FOR A PACER

[75] Inventor: Koen J. Weijand, Hoensbroek, Netherlands

[73] Assignee: Medtronic, Inc., Minneapolis, Minn.

[21] Appl. No.: 957,975

[22] Filed: Oct. 7, 1992

[51] Int. Cl.⁵ ............................................. A61N 1/36
[52] U.S. Cl. ...................................................... 607/21
[58] Field of Search ........................ 607/21, 17, 28, 9

[56] References Cited

U.S. PATENT DOCUMENTS

| | | |
|---|---|---|
| 3,057,356 | 10/1962 | Greatbatch . |
| 3,345,990 | 10/1967 | Berkovits . |
| 4,305,396 | 12/1981 | Wittkampf et al. . |
| 4,428,378 | 1/1984 | Anderson et al. . |
| 4,543,954 | 10/1985 | Cook et al. . |
| 4,556,063 | 12/1985 | Thompson et al. . |
| 4,688,573 | 8/1987 | Alt ........................ 607/21 |
| 4,729,376 | 3/1988 | DeCote, Jr. . |
| 4,750,495 | 6/1988 | Moore et al. . |
| 4,759,366 | 7/1988 | Callaghan . |
| 4,858,610 | 8/1989 | Callaghan et al. . |
| 4,878,497 | 11/1989 | Callaghan et al. . |
| 4,945,909 | 8/1990 | Fearnot et al. ..................... 607/21 X |
| 5,014,704 | 5/1991 | Alt ..................... 607/21 X |
| 5,042,480 | 8/1991 | Hedin et al. ..................... 607/21 X |
| 5,127,404 | 7/1992 | Wyborny et al. . |
| 5,176,137 | 1/1993 | Erickson et al. . |
| 5,176,138 | 1/1993 | Thacker . |

OTHER PUBLICATIONS

Philip et al., "Continuous Thermal Measurement of Cardiac Output", IEEE Transactions on Biomedical Engineering, vol. BME-31, No. 5, May 1984, pp. 393-400.

*Primary Examiner*—Lee S. Cohen
*Assistant Examiner*—Jeffrey R. Jastrzab
*Attorney, Agent, or Firm*—Reed A. Duthler; Harold R. Patton

[57] ABSTRACT

A pacemaker system which includes a fast responding temperature sensor located near the distal end of a transvenous pacing lead generates a cycle-by-cycle variation of temperature indicative of the mechanical pumping action of the heart. A timer is used to define a detection window after the generation of a pacing pulse. The occurrence of a detected depolarization within the detection window indicates that the pacing pulses capture the heart.

14 Claims, 4 Drawing Sheets

TEMPERATURE SENSOR BASED CAPTURE DETECTION FOR A PACER

BACKGROUND OF THE INVENTION

This invention relates to the implantable pacemakers and more particularly to a system for detecting the evoked response of the cardiac tissue shortly after the application of an electrical stimulation pulse.

DESCRIPTION OF THE PRIOR ART

The cardiovascular system provides oxygenated blood to various structures of the body. The body's demand for oxygenated blood is reflected by the rate at which the sinus node of the heart beats. The electrical signal generated by the sinus node causes the atria or upper chambers of the heart to contract, forcing blood into the lower chambers or ventricles of the heart. After a brief delay, the lower chambers of the heart contract forcing the blood throughout the body. The contraction of the ventricles proceeds in an organized fashion which is reflected by the passage of a depolarization wave front through the heart muscle.

Various disease mechanisms cause conduction disturbances which interfere with the natural conduction system of the heart. A variety of implantable medical devices have been developed to treat these abnormalities. The bradycardia pacemaker is an example of one such implantable medical device which supplies therapeutic stimulation to the heart to compensate for these conduction defects.

The modern pacer system comprises a catheter or lead system, and a pulse generator or pacer. The lead system is passed through a vein into the right ventricle of the heart. There are two forms of lead systems in common use. The first form is a unipolar lead which has a tip electrode located proximate the distal end of the lead. The pacemaker housing or can forms a reference electrode in this configuration. The second form of lead system is the bipolar lead which includes a tip electrode used in conjunction with a ring electrode located near the tip electrode. In either case, the distal end of the lead carries a tip electrode which contacts the myocardium. The proximal end of the lead is connected to the pulse generator. The pulse generator is usually implanted subcutaneously outside the rib cage.

The first pacemakers paced the heart at a metronomic rate independent of the heart's underlying rhythm. Such pacemakers are typified by U.S. Pat. No. 3,057,356 to Greatbatch. One problem with such pacemakers is that they may compete with the heart's underlying rhythm and provoke lethal arrhythmias.

The demand pacer was introduced to overcome this defect. This form of pacer contains circuitry to detect a depolarization of the cardiac tissue. The circuitry for performing this function is referred to as a sense amplifier in the art. The function of the sense amplifier is to generate a sense event signal which is used by the escape interval timer of the pacer to synchronize the pacer to the heart's rhythm. In operation the pacer escape interval timer is set to a nominal stimulation rate (standby rate) which reflects the lowest permissible heart rate. If the underlying heart rate is above the standby rate, the pacer detects the cardiac depolarization and prevents the delivery of pacing stimuli. This form of pacer is now classified as a VVI mode pacer and is taught to the art by U.S. Pat. No. 3,345,990 to Berkovitz. The efficacy and safety of this pacing modality requires reliable sensing of heart activity.

A DDD mode pacemaker senses electrical signals in both the atrium and ventricle of the patient's heart, and delivers an atrial pacing stimulus in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologic-based signals, such as signals from sensors for measuring temperature or oxygen inside the patient's heart or measuring the level of a patient's activity. These rate-responsive pacemakers are labeled VVIR for a single chamber version or DDDR for a dual chamber version. Examples of these rate-responsive pacemakers are as described by the following U.S. Pat. Nos.:

4,428,378 to Anderson et al (activity),
4,543,954 to Cook et al (temperature), and
4,750,495 to Moore et al (oxygen).

The temperature and oxygen sensor signals typically used for a rate-responsive function utilize a low pass filtered long-term averaged signal. High-frequency components are treated as noise, see for example, "Continuous Thermal Measurement of Cardiac Output," Phillip et al., IEEE Transaction on Biomedical Engineering, Volume BME31, No. 5, May 1984. This reference demonstrates a cardiac response with a fast-acting temperature sensor; filtering out and using the low-frequency component (under 0.04 Hz) for improved thermal dilution techniques for continuous cardiac output measurement.

In an effort to extend the useful operating life of pacemakers and to allow extraction of useful diagnostic information, it has been common in recent years to provide a programmable output stimulation pulse which permits the physician to select an output pulse energy which is known to be sufficient to capture the heart but which is below the maximum obtainable output energy. In operation the physician can conserve battery power and thus extend the useful life of the pacer by selecting an output pulse energy just above the stimulation threshold of the patient's heart.

It has also been proposed to automatically adjust the output energy level. U.S. Pat. No. 4,305,396 issued to Whitkampf, et al. teaches a pacer in which the pacemaker has its output energy automatically controlled in response to the detection of driven R-waves and its pacing rate varied as a function of the energy required to capture the heart. Practical realization of such systems has not occurred, because the pacer output stimulus which is delivered to the lead system is many orders of magnitude larger than the electrical signal generated by the heart and can mask detection of the evoked response or stimulated R-wave. However, this reference illustrates a longstanding desire for a practical detector system capable of reliably sensing an evoked response.

SUMMARY OF THE INVENTION

In contrast to the approach taken by the prior art, the present invention utilizes a fast responsive temperature sensor located proximal to the distal end of a transvenous pacing lead to monitor the intrabeat variation of venous blood temperature due to the pumping action of the heart. A signal indicative of the mechanical pumping action of the heart is detected and evaluated for sufficient magnitude to indicate a contraction subsequent to the occurrence of an output pacing stimulus.

Timer circuits coupled to the stimulating and detection circuits cooperate to define a capture detection window, initiated shortly after the delivery of a pacing pulse. The cardiac signal indicative of the cardiac pumping action occurring within this time window is defined as an evoked response. The occurrence or non-occurrence of an evoked response following a pacing pulse may be used to provoke a state transition in the pacer to alter its operation. For example, the amplitude or pulse width of the pacing pulse may be adjusted to provide reliable pacing at the minimum appropriate pulse energy level. Alternatively, the occurrence of the evoked response may be used for diagnostic purposes.

In a preferred embodiment of the pacer described herein, the detection of an evoked response is used to control the stimulation energy delivered by the pacer output stage. In general, the auto threshold pacer disclosed will minimize its output energy to maximize pulse generator longevity.

BRIEF DESCRIPTION OF THE DRAWINGS

The foregoing and other features of the present invention will be best appreciated with reference to the detailed description of a specific embodiment of the invention, which follows, read in conjunction with accompanying drawings wherein.

DETAILED DESCRIPTION OF THE PREFERRED EMBODIMENT

In the following description, reference is made to an illustrative embodiment for carrying out the invention. It is understood that other embodiments may be utilized without departing from the scope of the invention. For example, the invention is disclosed in the context of a VVI modality pacer for treating bradycardia. It should be appreciated that the technique for evoked response detection could also be applied to a dual chamber device where capture detection is used to control the energy of the pacing stimuli delivered to the atria. In a similar fashion the ability to detect the evoked response will find utility in tachyarrhythmia pacers where direct evidence that capture has occurred can be used as feedback to control the delivery of tachyarrhythmia therapies.

Figure 1:
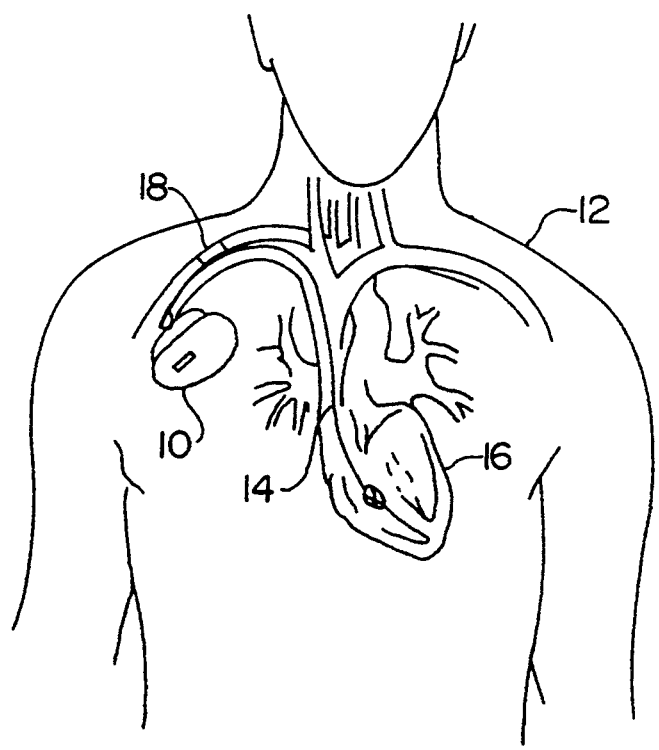
FIG. 1 is a diagram showing the placement in a patient of a pacemaker in accordance with the present invention.

The present invention will now be more fully described with reference to various figures of the drawings, FIG. 1 showing generally how a pacemaker 10 in accordance with the present invention may be implanted in patient 12. A pacemaker lead 14 is electrically coupled to pacemaker 10 and extends into the patient's heart 16 via a vein 18. The distal end of the lead 14 includes one or more exposed conductive electrodes for receiving electrical cardiac signals and for delivering electrical pacing stimuli to the patient's heart 16. In accordance with the invention to be hereinafter described, the distal end of the pacing lead 14 also incorporates a temperature transducer (not shown in FIG. 1 due to the small scale of that figure) for producing electrical signals representative of the temperature of the blood contained within the right ventricle of the heart 16.

Figure 2:
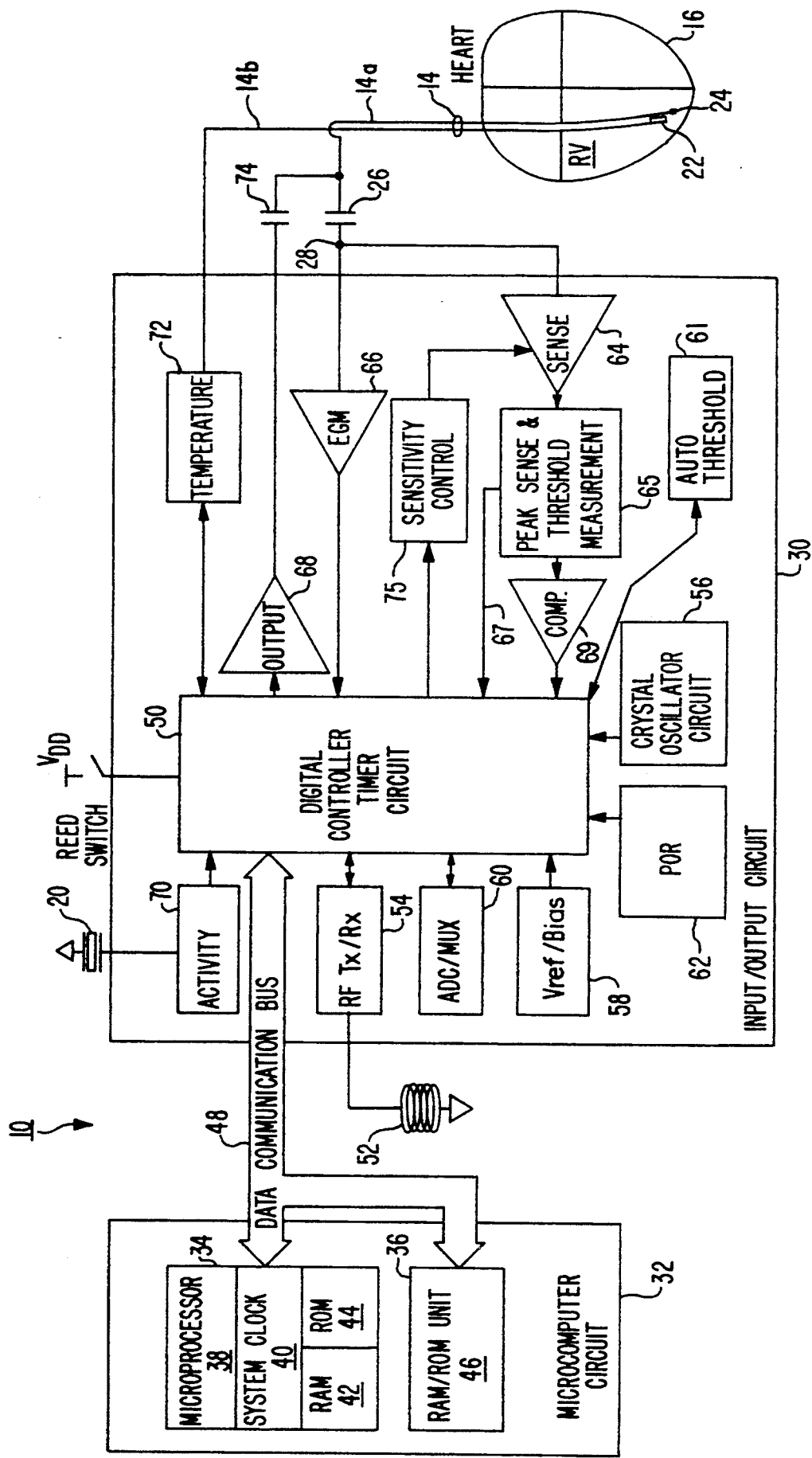
FIG. 2 is a block diagram of the circuitry of a pacemaker in accordance with an embodiment of the present invention.

Turning to FIG. 2, a block diagram of pacemaker 10 from FIG. 1 is shown. Although the present invention is described in conjunction with the pacemaker 10 having a microprocessor-based architecture, it will be understood that it could be implemented in any logic-based, custom integrated circuit architecture, if desired. It will also be understood that the present invention may be utilized in conjunction with other implantable medical devices, such as cardioverters, defibrillators, diagnostic monitoring devices, cardiac assist systems, and the like.

In the embodiment shown in FIG. 1, pacemaker 10 includes an activity sensor 20, which may be, for example, a piezoelectric element bonded to the inside of the pacemaker's housing. Sensor 20 provides a sensor output which varies as a function of a measured parameter that relates to the metabolic requirements of patient 12. In addition, pacemaker 10 includes a temperature sensor 22 disposed at the distal end of lead 14, as previously noted, which may be similarly used to ascertain the metabolic requirements and/or cardiac output of patient 12. The construction of the lead is not critical to the invention, various suitable lead arrangements being known to those skilled in the art. See for example, U.S. Pat. No. 4,543,954 to Cook, et al. and incorporated herein by reference.

Pacemaker 10 is schematically shown in FIG. 2 to be electrically coupled by a pacing lead 14 to a patient's heart 16. Lead 14 includes an intracardiac electrode 24 and temperature sensor 22 located near its distal end and positioned within the right ventricular chamber heart 16. Lead 14 can carry either unipolar or bipolar electrodes as is well known in the art. In the presently disclosed embodiment, lead 14 which couples pacemaker 10 to the ventricular endocardium can comprise a steroid-tipped, unipolar lead with an integral temperature transducer of the type describe in the aforementioned reference. Electrode 24 is coupled by a suitable lead conductor 14a through input capacitor 26 to node 28 and to input/output terminals of an input/output circuit 30. Output from the first sensor 20 is coupled to input/output circuit 30. Output from temperature sensor 22 is also coupled to input/output circuit 30 by a suitable lead conductor 14b.

Input/output circuit 30 contains the analog circuits for interface to the heart 16, first sensor 20, temperature sensor 22, and antenna 52, as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46. Microcomputer circuit 32 is coupled by data communication bus 48 to a digital controller/timer circuit 50. Microcomputer circuit 32 may be fabricated of custom integrated circuit devices augmented by standard RAM/ROM components.

It will be understood that the electrical components represented in FIG. 2 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programmer (not shown), is accomplished in the presently disclosed embodiment by means of data first being digitally encoded and then pulse position modulate on a damped RF carrier, as substantially described in co-pending U.S. patent application Ser. No. 07/468,407, filed on Jan. 22, 1990, entitled "Improved Telemetry Format," which is assigned to the assignee of the present invention and which is incorporated herein by reference.

A crystal oscillator circuit 56, typically a 32,768 Hz crystal-controlled oscillator, provides main timing clock signals to digital controller/timer circuit 50. A Vref/Bias circuit 58 generates a stable voltage reference and bias currents for the analog circuits of input/output circuit 30. An analog to digital converter/multiplexor (ADC/MUX) unit 60 digitizes analog signals and voltages to provide "real time" telemetry of temperature and intracardiac signals and battery end-of-life (EOL) replacement function. A power-on reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input-/output circuit 30.

Digital controller/timer circuit 50 is coupled to a sense amplifier 64 and an electrogram amplifier 66 for receiving amplified and processed signals picked up from electrode 24 through lead conductor 14a and capacitor 26 representative of the electrical activity of the patient's heart 16. Sense amplifier 64 amplifies sensed electrical cardiac signals and provides this amplified signal to peak sense and threshold measurement circuitry 65, which provides an indication of peak sense voltages and the measured sense amplifier threshold voltage on multiple conductor signal path 67 to digital controller/timer circuit 50. The amplified sense amplifier signal is also provided to a comparator 69. The electrogram signal developed by EGM amplifier 66 is used on those occasions when the implanted device is being interrogated by an external programmer (not shown) in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. Input/output circuit 30 further includes sensitivity control circuitry 75 coupled between digital controller/timer circuit 50 and sense amplifier circuit 64. Sensitivity control circuit 75 controls the sense amplifier gain and thus the sensing threshold of sense amplifier 64 as instructed by digital controller/timer 50. An output pulse generator 68 provides the pacing stimulus to the patient's heart 16 through coupling capacitor 74 in response to a pacing trigger signal developed by digital controller/timer circuit 50 each time the escape interval times out, or an externally transmitted pacing command has been received, or in response to other stored commands as is well known in the pacing art.

Digital controller/timer circuit 50 is coupled to an activity circuit 70 for receiving, processing, and amplifying signals received from activity sensor 20. Activity circuit 70 produces an activity signal which is representative of the patient's metabolic requirements. Similarly, the digital controller/timer circuit 50 is coupled to a temperature circuit 72 for receiving, amplifying and processing sensor output from temperature sensor 22. In the presently disclosed embodiment of the invention, temperature circuit 72 produces an amplified, filtered analog temperature signal which is received by digital controller/timer circuit 50. The design of the temperature sensing circuitry is not critical to the invention herein described, various suitable designs being known to those skilled in the art. See for example, U.S. Pat. No. 4,803,987 to Calfee, et al. and incorporated herein by reference. In conjunction with ADC/MUX 60, digital controller/timer circuit 50 samples and digitizes the temperature signal from the temperature circuit 72 to obtain the digital representation of the peak-to-peak value of the intracardiac blood temperature during each cardiac cycle. This value is provided to microprocessor 34, which maintains a running average over a previous number of cardiac cycles of the intracardiac pulse temperature.

Dynamic temperature sensor 22 is disposed in the right ventricle (RV) of the patient's heart to sense fluid temperature therein ($RV_{temp}$), and to provide a sensor output ($Output_{temp}$) related to changes in the fluid temperature associated with the heart's mechanical activity, contractility and blood flow. Processing by pacemaker 10 of $Output_{temp}$ yields a signal which is proportional to the magnitude of such RV temperature changes. Each sensed or paced RV event will yield a dynamically varying signal. In the preferred embodiment, the last sixteen valid pulse values (both paced and sensed events) are used to determine an average temperature pulse peak value, referred to as the temperature pulse peak average or "TEMP.AVG" Pacemaker 10 tests for validity of each peak temperature value on a sample-by-sample basis, based upon the requirement that a sampled temperature pulse peak value must be within a predetermined range defined by the TEMP.AVG value. In the preferred embodiment, this validity range is defined as temperature pulse peak values between 25% to 400% of TEMP.AVG. Values outside this validity range are considered artifacts and are ignored. Once determined, TEMP.AVG is used to verify capture on a beat-by-beat basis.

A programmable (25% to 75%, in 12.5% steps) threshold of TEMP.AVG value (a continuous running average of 16 pulse temperature values) during a window of time (T2) subsequent to a stimulating pulse will be used to generate a capture detect signal in response to a successful capture due to the stimulating pulse.

The capture detect signal is generated when the temperature circuitry 72 in conjunction with the microcomputer circuit 32 generates a detect signal during the capture detect window T2. This capture detect signal may be used in a variety of ways, and is illustrated herein in the context of an auto-threshold-type pacer. In this instance, the capture detect signal is communicated to auto-threshold logic 61. Auto threshold logic 61 controls the energy content of the pacing pulses delivered by the output circuit 68 to the lead system via capacitor 74. In the event that a pacing pulse is delivered and no capture detect signal follows, auto threshold logic 61 will generate a control signal allowing input/output circuit 30 to increment the amplitude of the pacing pulses provided by output circuit 68. Auto threshold logic 61 may also decrement the amplitude of the pacing pulses in response to an extended period in which all pacing pulses successfully capture the heart to enable a determination of the minimum energy required to reliably pace the heart. Auto threshold logic 61 may also respond to the failure of a pacing pulse to capture the heart by quickly triggering an additional pacing pulse at an increased amplitude.

Appropriate mechanisms for adjusting the energy content of the pacing pulses generated by output circuit 68 are disclosed in U.S. Pat. No. 4,858,610 issued to Callaghan et al., U.S. Pat. No. 4,878,497 issued to Callaghan et al., and U.S. Pat. No. 4,729,376 issued to Decote, all of which are incorporated herein by reference in their entireties. Alternative pacing functions which may be modified in response to the detection or nondetection of cardiac depolarizations during the capture detect window are described in U.S. Pat. No. 4,759,366 issued to Callaghan et al., and in the above cited U.S. Pat. No. 4,305,396 issued to Whittkampf, both of which are incorporated herein by reference in their entireties.

Figure 3:
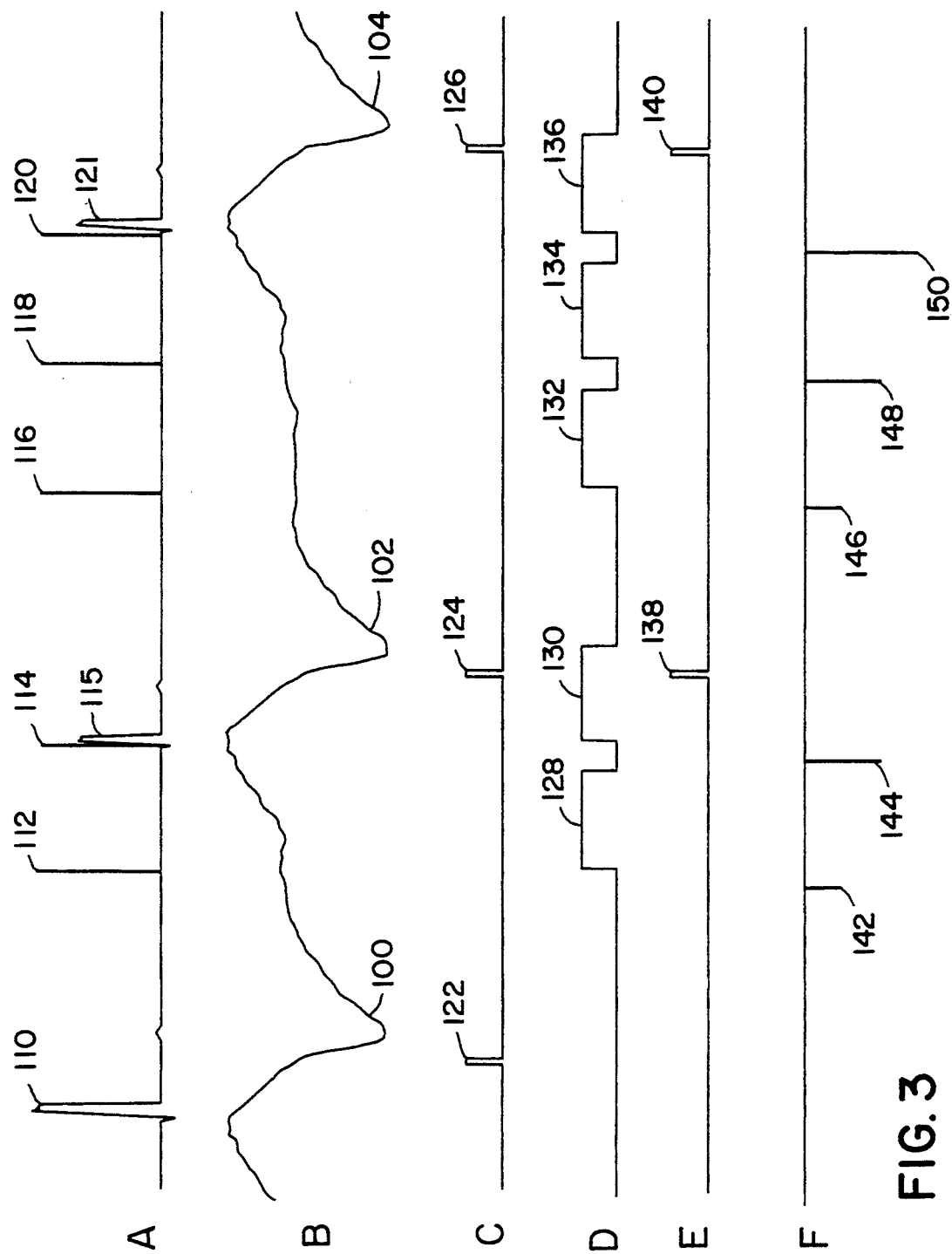
FIG. 3 is a timing diagram which reflects function of the invention.

The operation of the invention is illustrated in FIG. 3. This figure shows tracings of cardiac waveforms having a unipolar pacing lead implanted in the heart. Pacing pulses were delivered between the tip electrode and electrode corresponding to pacemaker 10 housing (FIG. 1).

Tracing 1 was taken with the sense amplifier 64 coupled to tip and can electrodes, and corresponds to the signals seen on the pacing lead 14.

Tracing 2 corresponds to the signal seen by the temperature circuit 72 from the sensor 22.

Tracing 3 reflects the logic level output of the peak temperature detect circuitry.

Tracing 4 corresponds to the capture detect window signal. High logic level signals in tracing 4 correspond to the duration of the capture detect window T2.

Tracing 5 corresponds to the logic level output of the evoked response detection circuitry and indicates the occurrence of a sensed ventricular depolarization during the T2 time window.

Tracing 6 corresponds to the output of the output circuit 68 (FIG. 2). The amplitude of the pacing pulses are reflected by the height of the pulse markers. The occurrence of pacing pulses is also reflected by the artifacts 112, 114, 116, 118 and 120 (tracing 1).

The first cardiac waveform 110 results from a normal sinus depolarization of the heart. The sensed detect signal 122 on tracing 3 reflects the normal detection of this event. In the context of the pacer of FIG. 2, this detected depolarization resets the escape interval timer contained within digital controller timer circuit 50. At the conclusion of the escape interval, timer 50 generates a V pace signal which triggers a ventricular pacing pulse from output circuit 68.

Artifact 112 and pacing pulse marker 142 on tracing 6 indicate the delivery of a pacing pulse. A capture detect window is defined thereafter as indicated at 128, on tracing 4. No depolarization results, as the pacing pulse is of insufficient amplitude to capture the heart.

This lack of capture is evidenced by the fact that no V sense detect signal follows the delivery of the pacing pulse at 112. In this instance, the auto threshold logic 61 (FIG. 2) generates another ventricular pacing pulse at a programmed upper rate limit interval as indicated by artifact 114. The amplitude of this pacing pulse is increased, as indicated by pacing pulse marker 144 in tracing 6.

In this instance the second pacing pulse captures the heart as evidenced by the depolarization waveform 115 on tracing 1. This ventricular depolarization was detected within the capture detect window 130 following the delivery of pacing pulse at 114, as evidenced by V sense detect signal 124 in tracing 3 and capture detect signal 138 in tracing 5.

The tracings associated with depolarization waveform 121 illustrates a sequence of three pacing pulses delivered at 116, 118 and 120. The first two pacing pulses (116 and 118) fail to capture the heart, as indicated by the absence of V sense detect signals and capture detect signals during capture detect window 132 and 134. Pacing pulse amplitude is increased with each pulse, as indicated by pacing pulse markers 146, 148 and 150 (all at the programmable upper rate limit interval). The third pulse delivered at 120 is successful in capturing the heart as indicated by V sense detect signal 126 and capture detect signal 140 during capture detect window 136.

In FIG. 3, the T1 period extends from the conclusion of ventricular pace signal depicted in the figure by pacing artifacts 112, 114, 116, 118 and 120. The duration of the T1 period should be short with an expected duration of 10-50 milliseconds. The duration of period T2 should be long enough to allow a detection of any pacemaker triggered cardiac response. The Inventor believes that 100 to 300 milliseconds is an appropriate duration for T2.

Figure 4:
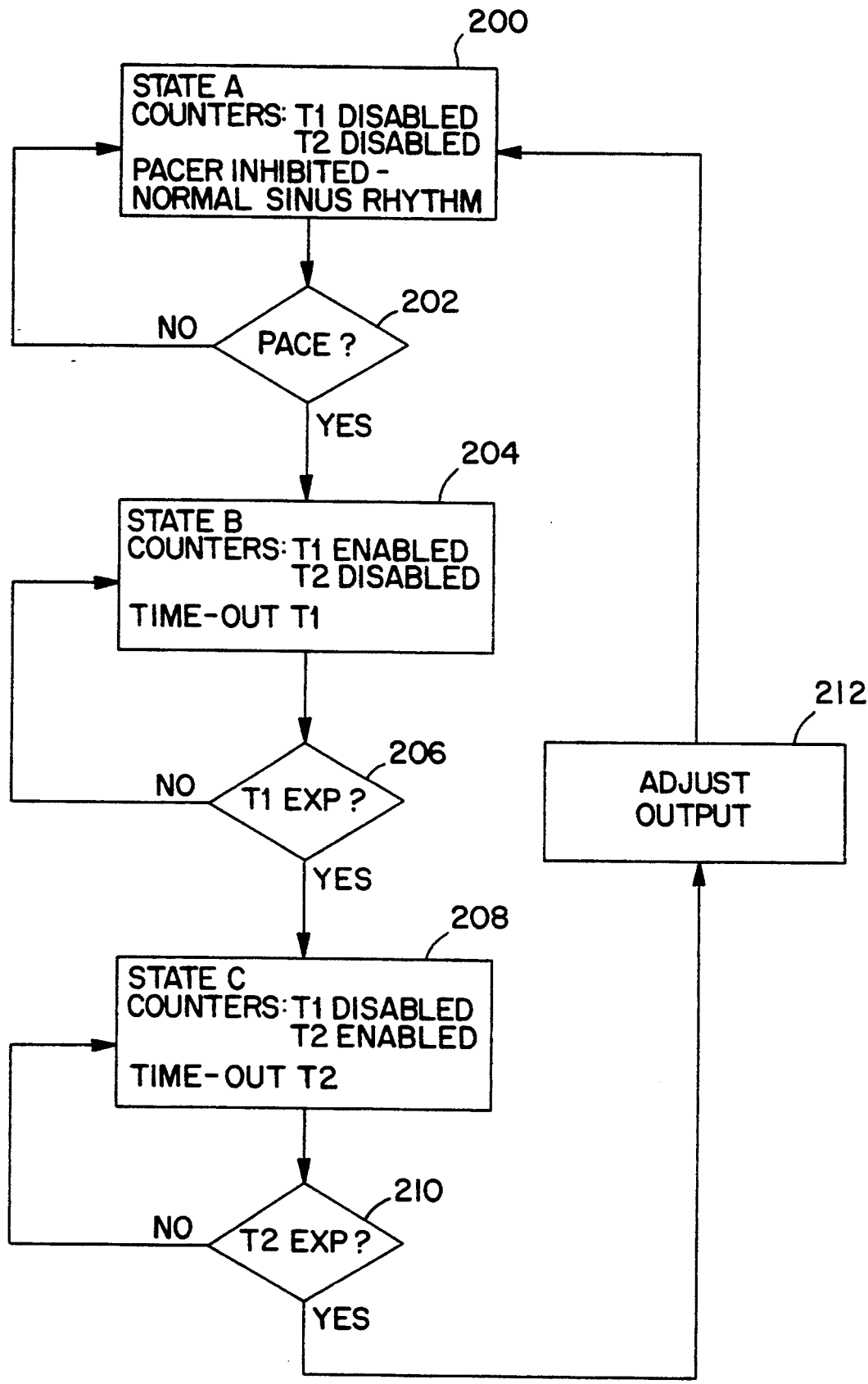
FIG. 4 is a machine description of the procedure for detecting the evoked response.

FIG. 4 shows a hardware flow diagram setting forth a state machine description of the detection procedure performed by the circuitry of FIG. 2.

In state A (200) shown in the flow diagram, both the T1 and T2 timing functions of the capture detection timer in digital controller timer circuit 50 are disabled. This state corresponds to the pacer's operation during sinus rhythm which inhibits the pacemaker. The state is reentered upon the occurrence of a V sense detect signal as at 122 in tracing 3.

The occurrence of a V paced signal at decision block 202 forces a state transition to state B (204) where the T1 timing function is enabled. As the period T1 times out the machine moves from state B (204) to state C (208) where the T2 window is being timed. The V sense detect signal occurs during T2 and is taken as the indication of an evoked response and a capture detect is declared in block 208. The expiration of the T2 time period, tested at decision block 210, triggers adjustment of the pacing pulse amplitude at 212 and the return to state A (200).

What is claimed:

1. An apparatus implanted within a patient for detecting an evoked response of cardiac tissue evoked by a pacing pulse, comprising:

pulse generator means for generating pacing pulses;
means for applying said pacing pulses to a heart;
sensing means for measuring blood temperature of said patient and for generating an electrical signal representative of said temperature;

monitoring means coupled to said sensing means for monitoring said electrical signal provided from said sensing means to detect an occurrence of a cardiac evoked response;

capture detect timer means for defining a capture detect window after the generation of a pacing pulse by said pulse generator means; and capture detect logic means responsive to said monitoring means and said capture detect timer means for detecting the occurrence of a said evoked response occurring within said capture detect window.

2. The apparatus of claim 1 wherein said capture detect timer means comprises:

a first timer means for defining a first time interval following the generation of said pacing pulse; and a second timer means for defining a capture detect window beginning with the expiration of said first time interval.

3. The apparatus of claim 2 wherein said first timer means comprises means for defining a first time interval of between 10 and 50 milliseconds.

4. The apparatus of claim 2 wherein said second timer means comprises means for defining a capture detect window of between 100 and 300 milliseconds.

5. The apparatus of claim 1 further comprising auto threshold logic means coupled to said pulse generator means and responsive to said capture detect logic means for altering energy content of said pacing pulses in response to an occurrence or non-occurrence of a detected cardiac evoked response within said capture detect window.

6. The apparatus of claim 5 wherein said auto threshold logic means comprises means for incrementing energy content of said pacing pulses in response to the non-occurrence of a detected cardiac evoked response within said capture detect window.

7. The apparatus of claim 1 or claim 2 or claim 3 or claim 4 or claim 5 or claim 6 wherein said sensing means comprises means for measuring blood temperature within said patient's heart.

8. A method of detecting an evoked response of a patient's cardiac tissue evoked by a pacing pulse, comprising:

generating pacing pulses;

applying said pacing pulses to said patient's heart;

measuring blood temperature of said patient and generating an electrical signal representative of said temperature;

monitoring said electrical signal to detect the occurrence of a cardiac evoked response;

defining a capture detect window after the generation of a pacing pulse; and detecting an occurrence of a said evoked response occurring within said capture detect window.

9. The method of claim 8 wherein said step of defining a capture detect window comprises:

defining a first time interval following the generation of said pacing pulse; and defining a capture detect window beginning with the expiration of said first time interval.

10. The method of claim 9 wherein said step of defining said first time interval comprises defining a first time interval of between 10 and 50 milliseconds.

11. The apparatus of claim 9 wherein said step of defining said capture detect window comprises defining a capture detect window of between 100 and 300 milliseconds.

12. The method of claim 8 further comprising altering energy content of said pacing pulses in response to an occurrence or non-occurrence of a detected cardiac evoked response within said capture detect window.

13. The method of claim 12 wherein said altering step comprises incrementing energy content of said pacing pulses in response to the non-occurrence of a detected cardiac evoked response within said capture detect window.

14. The method of claim 8 or claim 9 or claim 10 or claim 11 or claim 12 or claim 13 wherein said measuring step comprises measuring blood temperature within said patient'heart.

* * * * *